United States Patent [19] [11] Patent Number: 5,009,643
Reich et al. [45] Date of Patent: Apr. 23, 1991

[54] SELF-RETAINING ELECTRICALLY INSULATIVE TROCAR SLEEVE AND TROCAR

[75] Inventors: Harry Reich, Kingston, Pa.; Peter Koch, Schiller Park, Ill.

[73] Assignee: Richard Wolf Medical Instruments Corp., Rosemont, Ill.

[21] Appl. No.: 391,413

[22] Filed: Aug. 9, 1989

[51] Int. Cl.$^5$ .............................................. A61M 5/178
[52] U.S. Cl. .................................... 604/165; 604/167; 606/185
[58] Field of Search ................... 128/784, 4; 604/117, 604/164, 165, 167, 174, 264, 272; 606/108, 170, 185

[56] References Cited

U.S. PATENT DOCUMENTS

| 3,916,903 | 11/1975 | Pozzi | 604/164 X |
| 3,994,287 | 11/1976 | Turp et al. | 128/6 |
| 4,177,814 | 12/1979 | Knepshield et al. | 128/348 |
| 4,191,191 | 3/1980 | Auburn | 128/347 |
| 4,437,474 | 3/1984 | Peers-Trevartson | 128/784 |
| 4,491,126 | 1/1985 | Cullor | 128/1 |
| 4,498,902 | 2/1985 | Ash et al. | 604/164 |
| 4,622,968 | 11/1986 | Persson | 604/165 |
| 4,623,348 | 11/1986 | Feit | 623/11 |
| 4,627,838 | 12/1986 | Cross et al. | 604/105 |
| 4,654,030 | 3/1987 | Moll et al. | 604/165 |
| 4,655,752 | 4/1987 | Honkanen et al. | 604/256 |
| 4,670,008 | 6/1987 | Von Albertini | 604/165 |
| 4,685,904 | 8/1987 | Krebs | 604/164 |
| 4,755,173 | 7/1988 | Konopka et al. | 604/167 |
| 4,931,042 | 6/1990 | Holmes et al. | 604/164 |

FOREIGN PATENT DOCUMENTS 2218901 10/1973 Fed. Rep. of Germany .
2923105 12/1980 Fed. Rep. of Germany .
1103165 10/1955 France .
976972 12/1982 U.S.S.R. .
1287861 2/1987 U.S.S.R. .

OTHER PUBLICATIONS

"Trocar for Double Puncture", Karl Storz Sales Brochure, Page GYN 25, date unknown.
"Keene Self-Sealing Sleeve and Obturator", R. Wolf, p. AR20 Date unknown.

Primary Examiner—John D. Yasko
Assistant Examiner—Adam J. Cermak
Attorney, Agent, or Firm—Hill, Van Santen, Steadman & Simpson

[57] ABSTRACT

A trocar sleeve characterized by an annular flange adjacent a proximal end, a disc-shaped annular stop spaced from the annular flange in a distal direction and helically extending thread extending from said annular disc-shaped stop toward the distal end to prevent the removal of the sleeve from a puncture. The sleeve is used in conjunction with the trocar, which is provided with a disc-shaped annular stop between its ends, which engages the proximal end of the sleeve as the trocar is inserted therethrough and with cutting edges of the trocar being exposed to the distal end of the sleeve. The sleeve and trocar form a device which is used to form a puncture in the wall of a patient and then, after the distal end of the sleeve has been inserted in the puncture, the sleeve is rotated to thread the sleeve into the puncture to a position to prevent its removal. The sleeve is particular useful for the insertion of various instruments, such as endoscopes, to perform internal surgery and is, preferably, provided with an insulating inner sleeve layer.

9 Claims, 1 Drawing Sheet

5,009,643

SELF-RETAINING ELECTRICALLY INSULATIVE TROCAR SLEEVE AND TROCAR

BACKGROUND OF THE INVENTION

The present invention is directed to a self-retaining trocar sleeve and the sleeve in combination with a trocar.

In laparoscopy, it is desirable to have a sleeve member for penetrating through a wall of the abdomen and the peritoneum, which sleeve member will remain in place after withdrawing a trocar. Examples of such sleeves are disclosed in German No. OS 22 18 901 and German No. OS 29 23 105. In both of these sleeves, the outer surface is provided with retaining means, which is formed by a helical thread or wire on the outer surface, which has a pitch that allows screwing the trocar sleeve into the abdomen wall. Disadvantages of these sleeves are that they do not provide surfaces that are easily grasped by the operator when inserting the trocar and sleeve combination. Another disadvantage, particularly with the sleeve disclosed in German No. OS 22 18 901, is that the length is such that when performing certain operations, the length of the sleeve interferes with the area in which the operation is being conducted by the instruments inserted through the sleeve.

SUMMARY OF THE INVENTION

The present invention is directed to an improved retaining sleeve and the combination of the sleeve with a trocar, wherein the sleeve has a reduced length so that it is less apt to interfere with the operation of the instruments inserted therethrough. The sleeve also has a gripping arrangement to allow easy gripping of the sleeve and the trocar that is inserted therein during the step of penetrating the abdomen wall and peritoneum.

To accomplish these goals, the present invention is directed to a device comprising a trocar sleeve and a trocar received in the sleeve, said trocar sleeve having a distal end and a proximal end, said sleeve adjacent the proximal end having an enlarged annular flange and a small annular stop spaced toward the distal ends from said annular flange, said sleeve having means to prevent the removal of the sleeve member from the patient being disposed on an exterior surface of the sleeve to extend from said stop toward the distal end, which means is preferably a helical thread which, preferably, terminates inward from the distal end to provide a smooth portion of the sleeve adjacent the distal end. The trocar, which is used with the sleeve, has a distal end with a cutting edge, which is preferably formed by a pyramidal tip, and at a proximal end with a knob. The trocar has a stop which is disposed between the ends at a distance from the distal end and which is slightly greater than the length of the sleeve so that with the trocar inserted in the sleeve, with the stop of the trocar engaging the proximal end of the sleeve, the cutting edge of the trocar extends out of the distal end of the sleeve to enable piercing the abdomen wall during the step of inserting the sleeve.

Preferably, the sleeve is provided with an insulating inner layer to electrically insulate the metal of the sleeve from any instrument being inserted therethrough, and the annular flange is provided with knurlings or grooves to improve the grip thereon. Also adjacent the annular flange is a seal which will form a seal with an instrument inserted through the sleeve or with the trocar when inserted therethrough.

Other advantages and features of the invention will be readily apparent from the following description of the preferred embodiments, the drawings and claims.

DESCRIPTION OF THE PREFERRED EMBODIMENTS

Figure 3:
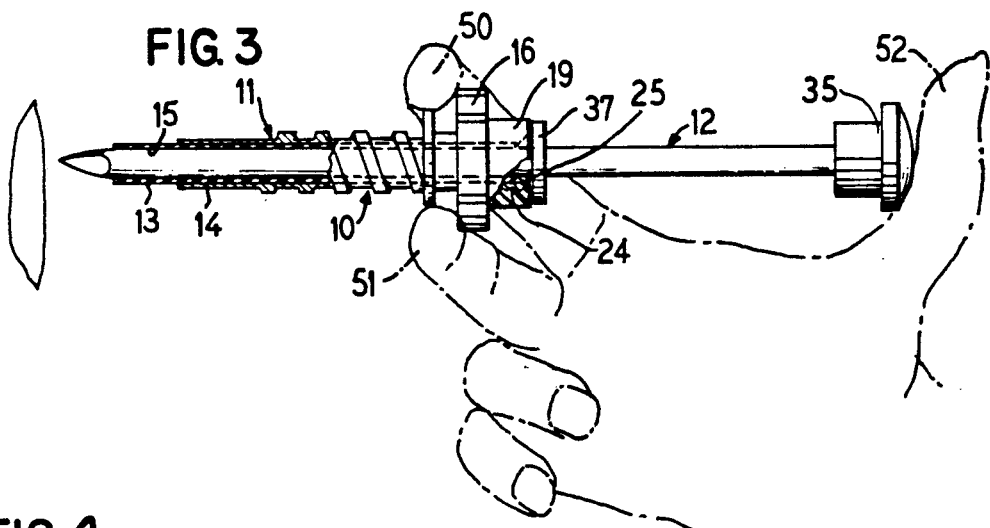
FIG. 3 is a combination of the sleeve and trocar, with portions of the sleeve broken away for purposes of illustration.

The principles of the present invention are particularly useful when incorporated in a device, generally indicated at 10 in FIG. 3, which device includes a trocar sleeve 11 and a trocar 12, which is inserted in the sleeve 11.

Figure 5:
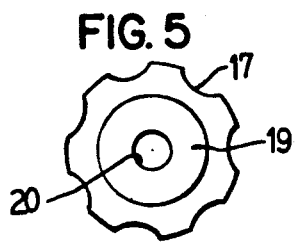
FIG. 5 is a right end view of the sleeve of FIG. 1.

The sleeve 11, at a distal end, has an electrically insulating sleeve 13 extending out of a metal sleeve 14. As illustrated in FIG. 3, this sleeve 13 extends the full length of the metal sleeve 14 and acts to insulate any instrument which is inserted through a bore 15 of the sleeve 11. Adjacent the proximal end, which is opposite the distal end, the sleeve 11 has an annular flange 16 which is provided with knurlings or notches 17 (best illustrated in FIG. 5) which improve the grip of the flange 16 when threading the sleeve, as discussed hereinafter. Spaced from the flange 16 in a direction toward the distal end is an annular flange forming an annular or disk-shaped stop 18. Between the flange 16 and the proximal end, the sleeve has a threaded projection which receives a seal cap 19. As best illustrated in FIG. 5, the seal cap 19 has a round or circular opening 20, which is of a diameter smaller than the instruments being placed through the sleeve and which seal 19 will, thus, form a seal with an instrument or the trocar 12 when inserted therethrough. The projection 24 has a conical countersink portion 25 that merges with the bore 15 and provides space for displacement of a portion of the seal cap 19 when the trocar 12 is inserted.

In order to retain the sleeve, it is provided with means to prevent removal of the sleeve, which means is illustrated as a helically wound thread 22 which begins adjacent the stop 18 and extends toward the distal end of the sleeve. As illustrated, it terminates from the distal end 23 of the metal sleeve to provide a region that is free of the threads.

Figure 1:
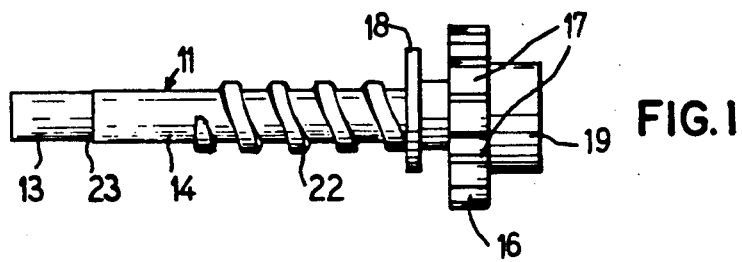
FIG. 1 is a side view of a trocar sleeve in accordance with the present invention.
Figure 2:
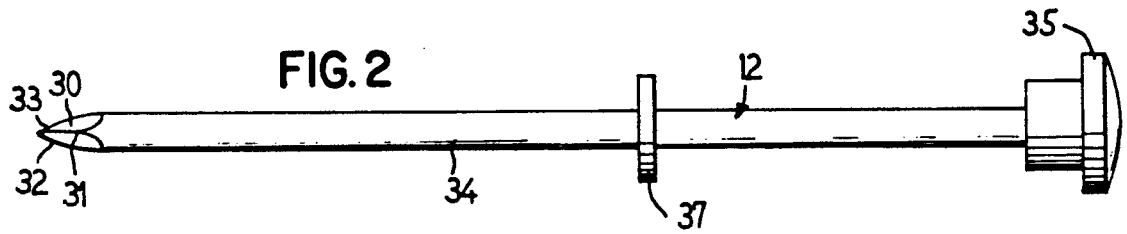
FIG. 2 is a side view of the trocar used with the sleeve of FIG. 1.

The trocar 12, as best illustrated in FIGS. 2 and 3, has a distal end provided with a pyramidal tip 30 which results in cutting edges 31, 32 and 33. The trocar 12 has a shaft 34 with a diameter that allows it to be inserted through the sleeve 11 and, at the proximal end, is provided with a knob 35 which has a smooth configuration to allow it to be engaged either by the physician's thumb, as illustrated in FIG. 3, or to provide a surface on which the palm of the hand may be pressed. The trocar is also provided with a stop 37 which is formed by an annular flange which is positioned between the distal and proximal ends and is spaced from the pyramidal tip by a distance sufficient to allow the tip to extend through the proximal end of the sleeve 11, as illustrated in FIG. 3, when the stop 37 is in contact with the proximal end of the sleeve, which is shown to be the portion carrying the seal cap 19.

Figure 4:
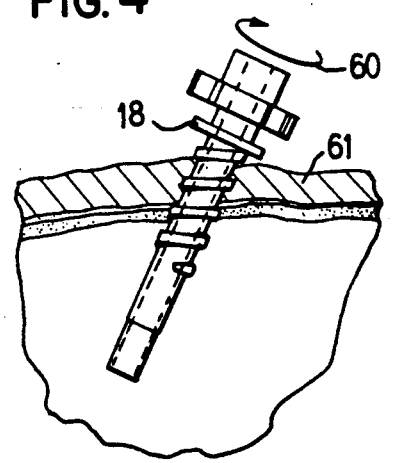
FIG. 4 illustrates the sleeve being threaded into an incision in the patient's abdomen.

When the device 10 is assembled, as illustrated in FIG. 3, it can be easily grasped by the physician with the index finger 50 and middle finger 51 on either side of the sleeve and engaging the flange 16 while a thumb 52 or palm of the hand is in contact with the knob 35. Thus, as illustrated, the device may be held in a manner similar to a hypodermic needle. In order to puncture the wall of the abdomen, the physician may cut or nick the skin with the scalpel and then with one hand raising or holding the skin of the abdomen in the area of the nick or incision where the trocar sleeve is to be inserted, he will then force the trocar through the incision of the skin to cause a perforation. With a little maneuvering of the device, the exposed portion of the inner sleeve 13 and the smooth portion of the metal sleeve 14 will enter the puncture in the manner of a dilator. At this time, the trocar 12 can be removed and then the sleeve can be inserted further until the threads come in contact with the edges of the perforation. At this time, the sleeve can be rotated in the direction of arrow 60 of FIG. 4 to cause the sleeve to be threaded into the perforation until the annular stop 18 engages the outer surface 61 of the skin. The provision of the knurls or notches 17 on the flange 16 aids in gripping the flange 16 for the purpose of rotating the sleeve on its axis to thread it into the perforation.

The sealing cap or member 19 is made of rubber and, as mentioned, has the circular opening 20, which is approximately 1 mm less in diameter than the diameter of the instrument, such as an endoscope or the diameter of the shaft 34 of the trocar 12. The insulating sleeve 13 is preferably made of fiberglass material and extends the full length of the sleeve. Preferably, the distance between the annular or disc-shaped stop 18 and the distal end of the insulating sleeve 13 is approximately 2¼ inches.

Although various minor modifications may be suggested by those versed in the art, it should be understood that we wish to embody within the scope of the patent granted hereon all such modifications as reasonably and properly come within the scope of our contribution to the art.

We claim:

1. A device comprising a combination of a trocar sleeve and a trocar received in the sleeve, said trocar sleeve having a distal end and a proximal end, said trocar sleeve including an insulative sleeve with an inner diameter extending through the trocar sleeve to insulate a metal portion of the trocar sleeve from an instrument being inserted through the trocar sleeve, said trocar sleeve, adjacent the proximal end, having an enlarged annular flange of a first diameter and a small annular stop with a second diameter less than the first diameter being spaced toward the distal end from said annular flange, said trocar sleeve having means to prevent the removal of the sleeve from a patient being disposed on an exterior surface of the sleeve to extend from said stop toward the distal end, said means comprising a helical thread extending from the stop toward the distal end and terminating prior to reaching said distal end so that a portion of the trocar sleeve at the distal end is free of said helical thread; said trocar having a distal end with a cutting edge and a proximal end with a knob, said trocar having a stop disposed between said ends and, at a distance from said distal end, which distance is slightly greater than the length of the sleeve so that with the trocar inserted in the sleeve with the stop of the trocar engaging the proximal end of the sleeve, the cutting edge of the trocar extends out of the distal end of the trocar sleeve.

2. A device according to claim 1, which includes a seal disposed on the proximal end of the trocar sleeve having a circular opening of a diameter less than the inner diameter of said insulative sleeve.

3. A device according to claim 2, wherein the annular flange of the trocar sleeve is provided with knurling to facilitate gripping the flange while rotating the trocar sleeve to thread it into a puncture of a patient's abdomen.

4. A device according to claim 1, wherein the annular flange is provided with knurling to facilitate gripping the flange to aid in rotating said sleeve for threading into a puncture.

5. A device according to claim 4, which includes a seal cap being disposed on the proximal end of said sleeve.

6. A trocar sleeve to provide a passage for inserting instruments during operations in an abdomen of a patient'body, said trocar sleeve comprising a first sleeve having a distal end and a proximal end, adjacent said proximal end said first sleeve having an annular flange with a first diameter, an annular disc-shaped stop with a diameter less than the first diameter being positioned on said sleeve adjacent the annular flange and spaced in the distal direction from said flange, means including a helical thread on an outer surface of the first sleeve adjacent said disc-shaped stop and extending toward said distal end to prevent removal of the trocar sleeve from a puncture in a wall of the abdomen, said trocar sleeve including an inner sleeve with an inner diameter extending the length of said first sleeve and being of an insulating material.

7. A trocar sleeve according to claim 6, which includes a seal cap disposed at the proximal end having a circular opening of a diameter less than the inner diameter of the inner sleeve, said edges of said opening providing edges for forming a seal with an instrument inserted through said trocar sleeve.

8. A trocar sleeve according to claim 7, wherein the annular flange is provided with knurling.

9. A device comprising a combination of a trocar sleeve and a trocar received in the sleeve, said sleeve having a distal end and a proximal end, said sleeve, adjacent the proximal end, having an enlarged annular flange of a first diameter and a small annular stop with a second diameter less than the first diameter being spaced toward the distal end from said annular flange, said sleeve having means to prevent the removal of the sleeve from a patient being disposed on an exterior surface of the sleeve to extend from said stop toward the distal end, said trocar sleeve including an inner sleeve of insulating material extending the length of said trocar sleeve and having an inner diameter, a seal cap being disposed on the proximal end of the trocar sleeve having a circular opening of a diameter less than an inner diameter of the inner sleeve and said annular flange having knurling to facilitate gripping said flange; said trocar having a distal end with a cutting edge and a proximal end with a knob, said trocar having a stop disposed between said ends and, at a distance from said distal end, which distance is slightly greater than the length of the sleeve so that with the trocar inserted in the sleeve with the stop of the trocar engaging the proximal end of the sleeve, the cutting edge of the trocar extends out of the distal end of the trocar sleeve.

* * * * *